(12) United States Patent
Reddy et al.

(10) Patent No.: US 9,376,771 B2
(45) Date of Patent: Jun. 28, 2016

(54) ANTIMICROBIAL MATERIALS AND COATINGS

(75) Inventors: Ganta S. Reddy, Cincinnati, OH (US); Jainagesh A. Sekhar, Cincinnati, OH (US)

(73) Assignee: MHI Health Devices, LLC, Cincinnati, OH (US)

( * ) Notice: Subject to any disclaimer, the term of this patent is extended or adjusted under 35 U.S.C. 154(b) by 1318 days.

(21) Appl. No.: 12/516,183

(22) PCT Filed: Nov. 27, 2007

(86) PCT No.: PCT/US2007/085564
§ 371 (c)(1),
(2), (4) Date: Jan. 11, 2010

(87) PCT Pub. No.: WO2008/136866
PCT Pub. Date: Nov. 13, 2008

(65) Prior Publication Data
US 2010/0136325 A1 Jun. 3, 2010

Related U.S. Application Data

(60) Provisional application No. 60/861,034, filed on Nov. 27, 2006.

(51) Int. Cl.
*C09D 5/16* (2006.01)
*D21H 21/36* (2006.01)
(Continued)

(52) U.S. Cl.
CPC .............. *D21H 21/36* (2013.01); *A01N 25/34* (2013.01); *A01N 59/16* (2013.01); *C09D 5/14* (2013.01);
(Continued)

(58) Field of Classification Search
CPC ........ D21H 21/36; C09D 5/1681; C09D 5/14; C09D 5/1625; C09D 5/1618; C09D 5/1687; A01N 59/16; A01N 25/34; A01N 59/00; A01N 59/20; Y10T 428/2982; Y10T 428/258; Y10T 428/256; Y10T 428/257; Y10T 428/25; Y10T 428/259
USPC ........................................ 428/323; 977/931
See application file for complete search history.

(56) References Cited

U.S. PATENT DOCUMENTS 5,681,575 A 10/1997 Burrell et al.
5,753,251 A 5/1998 Burrell
(Continued)

FOREIGN PATENT DOCUMENTS

WO WO-2007/114852 A2 10/2007

OTHER PUBLICATIONS

A. Yarnell, "Kitty Litter," Apr. 2004, Chemical & Engineering News (American Chemical Society), vol. 82, No. 17, p. 26, http://pubs.acs.org/cen/whatstuff/stuff/8217kitty.html.*
(Continued)

*Primary Examiner* — Nicholas Kokkinos
(74) *Attorney, Agent, or Firm* — Michael C. Connelly

(57) ABSTRACT

Durable antimicrobial coatings which may be deposited on a substrate. Such coatings may include a plurality of particles which are fused to the substrate and/or other particles. The particles may be provided using a single-sided electrode arrangement, which is configured to produce an electrical arc or discharge at one end of an electrode and to emit the particles from the electrode, where the arc or discharge can be produced without the end of the electrode being in proximity to a grounded object. The particles may be provided as one or more layers of nanoscale particles having an average size of less than about 1000 nm. Such coatings may have a thickness that is less than about 1000 nm. Thicker coatings may also be provided. The coatings may preferably include silver, tungsten, noble metals, nonstoichiometric compounds including ceramics, other metals including rare earth metals and compounds, and compositions thereof.

17 Claims, 13 Drawing Sheets

(51) Int. Cl.
*A01N 25/34* (2006.01)
*A01N 59/16* (2006.01)
*C09D 5/14* (2006.01)

(52) U.S. Cl.
CPC ............ C09D 5/1681 (2013.01); *C09D 5/1618* (2013.01); *C09D 5/1625* (2013.01); *C09D 5/1687* (2013.01); *Y10T 428/25* (2015.01); *Y10T 428/256* (2015.01); *Y10T 428/257* (2015.01); *Y10T 428/258* (2015.01); *Y10T 428/259* (2015.01); *Y10T 428/2982* (2015.01)

(56) References Cited

U.S. PATENT DOCUMENTS

| | | | |
|---|---|---|---|
| 6,238,686 B1 * | 5/2001 | Burrell et al. | 424/423 |
| 6,673,433 B1 * | 1/2004 | Saeki et al. | 428/323 |
| 6,734,157 B2 * | 5/2004 | Radwanski et al. | 510/439 |
| 7,880,119 B2 | 2/2011 | Ganta et al. | |
| 2004/0170822 A1 * | 9/2004 | Rohrbaugh et al. | 428/323 |
| 2005/0175649 A1 * | 8/2005 | Disalvo et al. | 424/401 |
| 2005/0267233 A1 | 12/2005 | Joshi | |

OTHER PUBLICATIONS

"Beidellite," 2001, Mineral Data Publishing (Handbook of Mineralogy), http://www.handbookofmineralogy.org/pdfs/beidellite.pdf.*
"Hectorite," 2001, Mineral Data Publishing (Handbook of Mineralogy), http://www.handbookofmineralogy.org/pdfs/hectorite.pdf.*
"Kaolinite," 2001, Mineral Data Publishing (Handbook of Mineralogy), http://www.handbookofmineralogy.org/pdfs/kaolinite.pdf.*
"Montmorillonite," 2001, Mineral Data Publishing (Handbook of Mineralogy), http://www.handbookofmineralogy.org/pdfs/montmorillonite.pdf.*
"Saponite," 2001, Mineral Data Publishing (Handbook of Mineralogy), http://www.handbookofmineralogy.org/pdfs/saponite.pdf.*
"Sauconite," 2001, Mineral Data Publishing (Handbook of Mineralogy), http://www.handbookofmineralogy.org/pdfs/sauconite.pdf.*
"Talc," 2001, Mineral Data Publishing (Handbook of Mineralogy), http://www.handbookofmineralogy.org/pdfs/talc.pdf.*
"Vermiculite," 2001, Mineral Data Publishing (Handbook of Mineralogy), http://www.handbookofmineralogy.org/pdfs/vermiculite.pdf.*
A. Janotti, C. G. Van de Walle, "Fundamentals of zinc oxide as a semiconductor," 2009 Reports on Progress in Physics, vol. 72, No. 12, http://iopscience.iop.org/0034-4885/72/12/126501.*
"Integral," obtained Feb. 16, 2013, Merriam-Webster, Inc., http://www.merriam-webster.com/dictionary/integral.*
"Silver (Ag) and water," obtained Feb. 16, 2013, Lenntech BV, http://www.lenntech.com/periodic/water/silver/silver-and-water.htm.*
"Solubility of Silver Compounds in water," obtained Feb. 16, 2013, Salt Lake Metals, http://www.saltlakemetals.com/Solubility_Of_Silver_Compounds.htm.*
L.C. De Jonghe, M.N. Rahaman, "Sintering of Ceramics," Handbook of Advanced Ceramics, http://home.agh.edu.pl/~nmos1/TPCP/TPCP-L8_TPCP_Sintering.pdf. Obtained Dec. 11, 2014.*
"Physics of Thin Films; Sputter Deposition Techniques," University of Colorado, Colorado Springs, http://www.uccs.edu/~tchriste/courses/PHYS549/549lectures/sputtertech.html. Obtained Dec. 11, 2014.*
"International Application Serial No. PCT/US2007/085564, International Search Report mailed Feb. 27, 2009", 3 pgs.
"International Application Serial No. PCT/US2007/085564, Written Opinion mailed Feb. 27, 2009", 6 pgs.

* cited by examiner

Table 2B. Further Microbial Test Results for Certain Coated and Uncoated Substrates of Table 2A

| Expt# | Volume fraction at specified hour of incubation | % Destroyed | Picture showing # of bacteria (or None) at a specified hour of incubation | Picture showing # of bacteria (or None) at a specified hour of incubation | Picture showing # of bacteria (or None) at a specified hour of incubation |
|---|---|---|---|---|---|
| 207-5T | | | SS/ X-Cu5T/ SW/ 3:00/ SWAB/ INCUB/ COUNT | | |
| 211 | | | SS/ No deposit/ SW/3:00Hours/ SWAB/ INCUB/ COUNT | | |
| 213 | 4131.12 @ 116 h | Base | SS/ No deposit/ SW/ No-HGA/ 0:52mts/ SWAB/ INCUB/ COUNT | | |
| 208-5T | 82.90 | @ 27 h 13.9% Increased | SS/ X-Al/ SW/ 68:00 Hours / SWAB/INCUB/COUNT | | |
| 214 | 72.74 27 h | @ Base | SS/ No dep/ SW/ 68:00Hours/ SWAB/INCUB/COUNT | | |
| 209-5T | 25.50 @ 27 h | 64.9% Destroyed | SS/ X-SiC5T/ SW/ 64:30 Hours:Mins/ SWAB/ INCUB/ COUNT | | |
| 210-2T | 49.18 | @27 h 32.4% Destroyed | SS/ X-Cu2T/ SW/ 64:30 Hours:Mins/ SWAB/ INCUB/ COUNT | | |
| 215-5T | | | SS/ X-C-2T/ Culture/ 00:00? H/ SWAB/ INCUB/ COUNT | Abandoned | |

FIG. 11

| Expt# | Volume fraction at specified hour of incubation | % Destroyed | Picture showing # of bacteria (or None) at a specified hour of incubation | Picture showing # of bacteria (or None) at a specified hour of incubation | Picture showing # of bacteria (or None) at a specified hour of incubation |
|---|---|---|---|---|---|
| 216-5T | | | | | |
| 217-5T | | | None at 44:00 (Hours:Mins) but one white cotton fungus morphology of 1 cm dia present | None at 92:00 & 212:00 Hours:Mins. | |
| 218-5T | | | 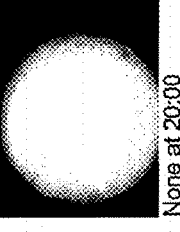 None at 21:10 | None at 44:00 & 92:00 & 212:00 Hours:Mins. Clean & no bacteria. | |
| 219-5T | | | 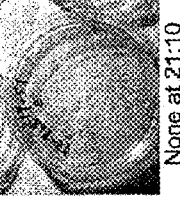 None at 20:00 | None at 20:00 | At 212:00 (Hours:Mins) two white & one black fungus |
| 220-5T | | | None at 21:10 | None at 44:00 (Hours:Mins) | At 140:00 (Hours:Mins)Red big size dots & fine dots |

FIG. 12

| Expt# | Volume fraction at specified hour of incubation | % Destroyed | Picture showing # of bacteria (or None) at a specified hour of incubation | Picture showing # of bacteria (or None) at a specified hour of incubation | Picture showing # of bacteria (or None) at a specified hour of incubation |
|---|---|---|---|---|---|
| 225 | | | | | Dishful of red bacteria dots at 68:30 Hours:Mins. At 236:40 (Hours:Mins) Dishful of red bacteria. |
| 226 | | | 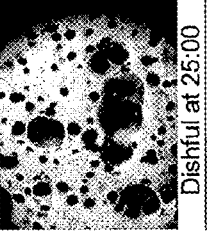 Dishful at 25:00 | 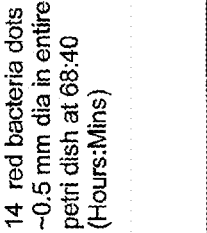 Dishful at 25:00 14 red bacteria dots of ~0.5 mm dia in entire petri dish at 68:40 (Hours:Mins) | At 236:40 (Hours:Mins) `11 red bacteria dots |
| 226-R | | | 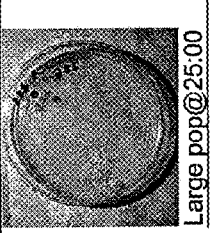 11 red dots at 46:10 | | |
| 227 | | | None at 20:30 | Large pop@25:00 |  Large pop@43:00 At 165:30 (Hours:Mins)four large size fungus black color |
| 228 | | | None at 21:30 | | At 140:00 (Hours:Mins) diskfull of small red bacteria |

FIG. 13

| Exp# | Volume fraction at specified hour of incubation | % Destroyed | Picture showing # of bacteria (or None) at a specified hour of incubation | Picture showing # of bacteria (or None) at a specified hour of incubation | Picture showing # of bacteria (or None) at a specified hour of incubation |
|---|---|---|---|---|---|
| 218-5T-2H-28H | | | | | At 111:30 (Hours:Mins) ~12 black & one red fungus |
| 220-5T-2H-28H | | | | | At 111:30 (Hours:Mins) ~12 black 7 one white fungus |
| 228-2H-28H | | | | | At 111:30 (Hours:Mins) ~12 black color fungus |
| X243 | | | 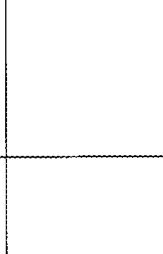 None at 24:00 | 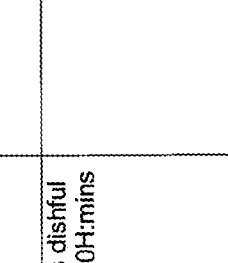 1/2 Dishful @ 37:30 | 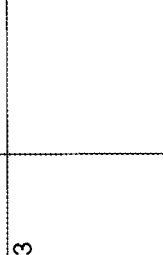 1/2 Dishful @ 37:30 |
| X244 | (i) Fine red dots dishful bacteria at 37:30H:mins (11/2; 8:00 am) | | 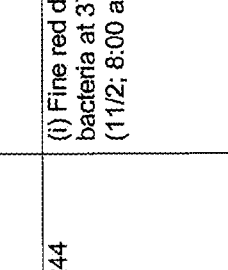 Dishful at 24:00 |  Dishful at 24:00 | 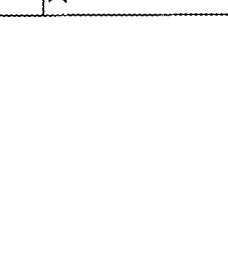 Dishful at 37:30 |

FIG. 14

Table 3B. Further Microbial Test Results for Certain Coated and Uncoated Substrates of Table 3A

| Expt# | # of colonies as counted in each frame of microstructure at 40X (22h of incubation) | # of colonies as counted in each frame of micro at 40X (24 h of incubation) | # of colonies as counted in each frame of microstructure at 40X (26 h of incubation) | # of colonies as counted in each frame of microstructure at 40X (39 h of incubation) | Picture showing # of bacteria (or None) at a specified hour of incubation |
|---|---|---|---|---|---|
| X235-5T | 0,0,0,0,0,0 | 0,0,0,0,0,0 | 0,0,0,0,0,0 | 0,0,0,0,0,0 | 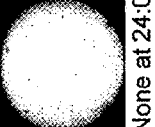 None at 24:00 |
| X237-5T | 3,1,2,1,3,1,1 | 3,3,0,1,3,3 | 3,3,3,5,3,2 | 3,4,3,4,5,4 |  Few at 24:00 |
| X239-5T | 0,0,0,0,0,0,0 | 0,0,0,0,0,0 | 0,0,0,0,0,1 | 0,0,0,1,0,0 (Very few ~125 in total of PD) | 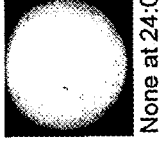 None at 24:00 |
| X245-5T | 2,5,4,2,2,3 | 4,5,5,6,4,5 | 3,6,7,6,6,2 | 5,6,6,6,6,9 | 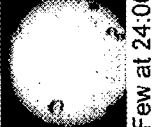 Few at 24:00 |

FIG. 15

| Expt# | # of colonies as counted in each frame of microstructure at 40X (22h of incubation) | # of colonies as counted in each frame of micro at 40X (24 h of incubation) | # of colonies as counted in each frame of microstructure at 40X (26 h of incubation) | # of colonies as counted in each frame of microstructure at 40X (39 h of incubation) | Picture showing # of bacteria (or None) at a specified hour of incubation |
|---|---|---|---|---|---|
| X247-5T | 4,1,5,3,6,3 | 2,4,3,4,5,0,3 | 5,4,5,6,5,5 | 4,6,5,5,5,7 | 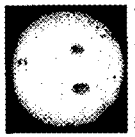 Few at 24:00 |
| X249-5T | 0,0,0,0,0,0 | 0,0,0,0,0, 0,0,0 | 0,0,0,0,0,0,3,0,0 | 0,0,1,0,0,0 (Very few ~250 in total of PD) | 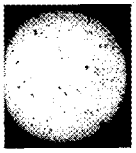 None at 24:00 |
| X251-5T | 1,4,3,1,3,0 | 3,1,0,1,3,3,2,2 | 3,1,2,2,1,3,4,3 | 1,4,4,3,4,1,1 |  Few at 24:00 |
| X252-5T | 4,6,4,6,6 | 6,7,3,7,10,5,6 | 7,8,8,10,6,8,7 | 7,8,11,7,6,5,9 |  Few at 24:00 |

FIG. 16

| Expt# | # of colonies as counted in each frame of microstructure at 40X (22h of incubation) | # of colonies as counted in each frame of micro at 40X (24 h of incubation) | # of colonies as counted in each frame of microstructure at 40X (26 h of incubation) | # of colonies as counted in each frame of microstructure at 40X (39 h of incubation) | Picture showing # of bacteria (or None) at a specified hour of incubation |
|---|---|---|---|---|---|
| X253-5T | 4,4,6,5,5 | 6,7,10,9,8,5 | 5,3,8,9,6,6,6 | 11,9,13,9,8,8 |  Few at 24:00 |
| X254 | 13,9,9,10,10 | 9,10,12, 10,12,12 | 10,11,16,9,10,12, 11 | 13,10,12,13,13,14 | 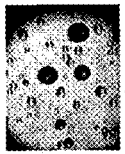 Dishful at 24:00 |

FIG. 17

ANTIMICROBIAL MATERIALS AND COATINGS

RELATED APPLICATIONS

This application is a U.S. National Stage Filing under 35 U.S.C. 371 from International Application No. PCT/US2007//085565, filed on Nov. 27, 2007 and published in English as WO 2008/136866 on Nov. 13, 2008, which claims the priority of U.S. Provisional Application No. 60/861,034, filed on Nov. 27, 2006, which are incorporated by reference herein in their entireties.

FIELD OF THE INVENTION

The present invention relates to materials having durable surfaces and coatings which can exhibit antimicrobial properties and other desirable characteristics.

BACKGROUND

Microbes may often be present on many common objects and surfaces in everyday life. Microbes can include, for example, bacteria, fungi, spores, viruses, prions, microorganisms such as, e.g., *Mycobacterium tuberculosis, listeria monocytogenas, escherichia coli, pseudomonas aeruginosa, salmonella typhimurium, salmonella enteritidis, delegionella bacteria, Yersinia pestis, staphylococcus aereus, bacillus subtilis, enterobacter aerogenes, streptococcus faecalis, legionella pneumophila, viibrio parahaemolyticus, bacillus cereus*, and other gram positive and gram negative microorganisms. Several such microbes/microorganisms, individually or in combination, can cause illness or other health problems, for example, when they come into contact with humans and/or animals, or when they are ingested along with food which has contacted them.

Surfaces can be treated using various techniques to reduce or eliminate the presence of microorganisms. Such cleaning, disinfecting, or "sterilization" techniques can be performed, e.g., using chemicals (for example, by application of disinfectant sprays or solutions), heat, steam, pressure, ultraviolet light or other radiation, etc., or combinations of such techniques. Disinfection of surfaces to reduce or eliminate a presence of microorganisms can be non-permanent, costly, inconvenient, ineffective, and/or time-consuming.

There is an increasing need for "antimicrobial" materials and surfaces which may be capable of killing such microbes/microorganisms and/or inhibiting growth or spreading thereof.

Certain industries, such as the health care and medical industry, may have a particular need for micro-organism-resistant surfaces. For example, hospitals and other medical facilities may have a particular need for sterile and uncontaminated surfaces, both in surgical areas as well as in convalescence facilities, where patient exposure may be significant and resistance to such microbes may be lowered. Much time and effort can be spent, for example, on sterilizing medical instruments, testing devices, etc. Often, such devices can be provided with disposable components or covers (e.g., disposable thermometer probes) to avoid cross-contamination between patients. Disposable needles are also commonly used. Such disposable materials involve increased costs and increased waste, as well as potential safety issues associated with their disposal.

The food-preparation and delivery industry is another area in which presence of microbes (e.g., bacteria) can be problematic. Food preparation facilities, if contaminated with microbes, can lead to contamination of food which may cause health problems when ingested. For example, restaurants, food manufacturing plants, and even home kitchens can contain preparation surfaces, utensils, and equipment which may contaminate food that comes into contact with them. There may be, for example, a particular need for reducing a presence and spreading of microbes in meat packaging plants.

Public and private facilities such as, e.g., restrooms, may also contain surfaces which can harbor and spread microbes, leading to potential health problems. To address this issue, products such as antimicrobial soaps and air dryers for hands may be offered, as well as disposable paper towels. Nevertheless, microbes may still be harbored on such objects as faucet and toilet handles, door knobs, keys, dispenser levers, etc.

In the transportation industry, including land, sea, air, and space vehicles, there may also be particular surfaces which can harbor and spread microbes, leading to potential health problems. For example, rental cars may benefit from durable antimicrobial surfaces (both interior and exterior). In particular, isolated environments such as, e.g., airplanes and submarines can also be safer if provided with antimicrobial surfaces.

Other common objects may benefit from antimicrobial surfaces, which can inhibit or prevent spread of microorganisms between people and/or animals that come into contact with such objects. For example, musical instruments, such as harmonicas, flutes, clarinets, etc., computer peripherals, communications equipment such as, e.g., telephones, pet accessories such as leashes and carriers, and/or other common household objects could benefit from antimicrobial surfaces.

Microbes can be present on a wide variety of materials and surfaces. Porous surfaces and surfaces which may often be damp or wet can provide moisture, nutrients, and/or other conditions which may promote growth and spreading of microbes. Common porous surfaces can include, e.g., kitchen sponges, cutting boards, and the like. Even metallic materials (e.g., stainless steel) can have small crevices and ridges which can foster growth of microbes. Thus, items such as medical instruments and kitchen utensils may present health problems if not properly and frequently cleaned, disinfected, and/or sterilized. Objects provided in hospitals, sterile laboratories, and other such "clean" facilities, including medical instruments, autoclaves, sterilizers, etc., may particularly benefit if provided with durable antimicrobial surfaces.

Certain materials and procedures have been developed to reduce or prevent a presence of microbes on certain surfaces. For example, compounds which may exhibit antimicrobial activity such as, e.g., certain salts or nanoparticles of silver, can be applied to certain substrates. Such antimicrobial coatings may be capable of killing or inhibiting growth of certain microbes. Application of such antimicrobial coatings may often be performed using solution chemistry or by combining antimicrobial compounds with polymers, resins, or other materials to coat a surface, where such materials may often be at least partially organic. However, such coatings may have limited lifetimes for killing or inhibiting growth of microbes. More importantly, such coatings may often not adhere well to the substrate, or they may only adhere to certain types of substrates. Further, such antimicrobial coatings may wear off to some degree when exposed to various environments or conditions (e.g., heat, abrasion, chemicals). Such wear, which can occur rapidly, may reduce or eliminate the ability of these coatings to kill or inhibit growth of microbes over time.

Thus, there may be a need for improved antimicrobial surfaces, coatings, and materials which are durable and effective in killing or inhibiting growth of microbes such as bacteria and other microorganisms. Further, there may be a need to provide such materials and coatings which are easy and relatively inexpensive to produce, and which may be applied to a broad variety of substrates. In addition, there may be a need for such antimicrobial coatings which can be applied to objects that are already in use or that are in need of repair.

SUMMARY OF EXEMPLARY EMBODIMENTS OF THE INVENTION

The exemplary embodiments of methods and materials according to the present invention can provide one or more durable coating layers of closely spaced, but partially separated (e.g., not fully sintered) small particles on a substrate which can exhibit antimicrobial properties, and method and apparatus for producing such coatings. For example, such particles may have an average size that may be less than about 1000 nm, less than about 800 nm, or preferably less than about 500 nm, or more preferably less than about 200 nm. The particles may have a shape that is approximately, spherical, cylindrical, acicular, or a mixture of these geometries. Such coatings can have a thickness that is less than about 1000 nm, or preferably less than about 800 nm, or less than about 500 nm. Thicker coatings may also be provided.

For example, a coating of small particles may be provided on a substrate using a single-sided electrode arrangement, which can include a power generator, a Pi circuit or equivalent circuit, and an electrode. The power generator can be a high-frequency generator. The electrode may have a form of a rod or wire, and may include $SiO_2$, $Si_3N_4$, SiC, Ag, W, Mo, Fe, C, and/or $MoSi_2$, and may further include a coating which includes silica or another oxide. In one exemplary embodiment of the present invention, the electrode may include silver or tungsten. The electrode may have a form of an electrically conductive rod coated with a mixture of a less conductive material such as, e.g., $SiO_2$, $SiO_x$, $Si_3N_4$, SiC, $Al_2O_3$, and/or $Mo(Al_x)Si_2$ (where x may have non-integer values representing a non-stoichiometric composition). Such electrode coating may contain various silicides such as, for example, molybdenum silicide (in one or more possible oxidation states which can be collectively represented by the formula $MoSi_2$). Alternatively, the electrode may include a nonconductive material that is coated with a conductive material such as, e.g., a metal or alloy. For example, such exemplary electrode can include, e.g., a silica material coated with gold. Alternatively, an exemplary electrode may comprise a conducting oxide such as, e.g., tin oxide, iridium oxide, nickel ferrite, etc.

The coating may be provided by producing an arc discharge at a distal end of the electrode, and placing the surface to be coated in proximity to the arc. The arc may be continuous, and it can be formed in the absence of a nearby object that is electrically grounded. Particles produced by an interaction between the arc and the electrode material can generate a discharge of particles which may impinge on the surface and adhere to it.

When the particles impinge they can be liquid particles or solid particles.

The exemplary particles may include metals such as, e.g., silver, tungsten, iron, copper, aluminum, or nickel, or combinations thereof, including alloys or mixtures of two or more such metals. The particles may further include oxygen, nitrogen, silicon, sulfur, fluorine or other halogens, silica, aluminum, silicon nitride, carbon, silicon carbide, phosphorous, iron oxide, as well as mixtures or combinations thereof. The small particles which can form the coating may be unsintered or only partially sintered, and can be at least partially adherent to adjacent particles and/or the substrate, and they may retain an open porous structure even at high temperatures. The particles can also remain adherent to the substrate and may resist removal from the substrate by abrasion or exposure to chemicals or other substances. The surface area density of the surface coated with small particles may be approximately 3 or 4. For example, conductive lubricating particles such as, e.g., molybdenum sulfide or graphite can be used, where such particles may provide an antibacterial lubricant surface. For example, particles which may be used to form antimicrobial surfaces or materials in accordance with exemplary embodiments of the present invention can include, e.g., noble metals, rare earth metals, Ba, Pb, Po, U, Ge, Ar, Se, In, all noble materials, Si, Al, Sn, Sb, Sr, Ni, Be, Co, C, Mg, Mo, V, Mn, Cu, Pd, Hf, La, Ta, Cd, S, P, Nb, $V_2O_5$, $Fe_2O_3$, $Fe_3O_4$, NiO, $MnO_2$, $SiO_2$, $MoO_3$, $HfO_2$, $WO_3$, $TiB_2$, $CrO_3$, $Nb_2O_5$, $Al_2Zr$, $B_4C$, $SiO_2$, $ZrSiO_4$, $B_2O_3$, CdS, MnS, MoS2, $NAN_3$, NaCN, $Si_2N_4$, PbO, $PbO_2$, $WO_2$, $BaO_2$, $SiO_x$, $TiO_x$, carbon-based nanotubes and mixtures or combinations of the above, as well as non-stoichiometric compound variations such as those which contain, e.g., fluorides, carbides, oxides, borides, phosphides, carbides and/or nitrides of the metals above.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 11 is Table 2B reporting further microbial test results for certain coated and uncoated substrates of Table 2A.

FIG. 12 is a continuation of Table 2B.

FIG. 13 is a further continuation of Table 2B.

FIG. 14 is a further continuation of Table 2B.

FIG. 15 is Table 3B reporting further microbial test results for certain coated and uncoated substrates of Table 3A.

FIG. 16 is a continuation of Table 3B.

FIG. 17 is a further continuation of Table 3B.

Figure 1:
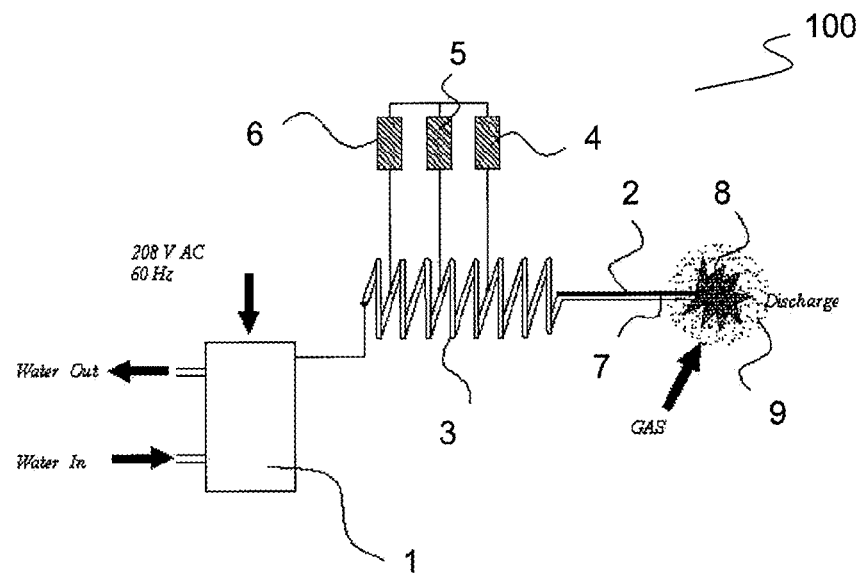
FIG. 1 is an illustration of an exemplary apparatus which may be used to produce antimicrobial materials in accordance with certain exemplary embodiments of the present invention.

Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures.

DETAILED DESCRIPTION OF EXEMPLARY EMBODIMENTS OF THE INVENTION

Exemplary embodiments of the present invention can provide durable antimicrobial surface coatings on a variety of substrates. Such coatings can include, e.g., microscopic and/or nanoscale particles of certain materials which may be strongly bonded to a substrate and/or to each other. The coatings may be porous or otherwise not fully sintered or densified.

Such coatings may be applied using exemplary techniques described, e.g., in U.S. patent application Ser. No. 11/098,474 and International Patent Application No. PCT/US06/60621, the entire disclosures of which are incorporated herein by reference in their entireties. Such exemplary techniques which may be used to provide coatings of small particles are described in more detail herein, and can be used to provide coatings or materials which surprisingly exhibit antimicrobial properties.

In this invention a one sided discharge is taught where such a discharge allows either heat or particles from the discharge to become available for welding. In such a method, welding can be effectively carried out in a micro or large scale. The particles can act as the filler material thus reducing the need for more fillers. In this manner heat and mass can be usefully and simultaneously transferred to a workpiece.

The singular aim of the invention is to create an extremely high potential localized point in a material which will continuously disintegrate and discharge when it experiences very high frequency alternating (sine wave type) current, thus producing heat and heated mass either during or subsequent to the discharge. This is called a once sided electrode method. No second electrode is required. If a work-piece is involved such as for example a welding fixture or a substrate to be coated, it does not have to be grounded in any manner. The discharge can take place to open air or gas or any other dielectric fluid which has a low electrical conductivity. The alternating current can have a variety of other frequencies superimposed on (Fourier deconvolution).

By creating an immense potential point, an unstable situation is created which can lead to a metallic discharger apparatus proposed herein or the proposed method of discharger.

The basic theory of operation of the metallic discharger is as follows: The metallic discharger can be created with the use of a modified high powered high frequency generator having a frequency preferably, but not limited to, in the range from 0.001 to 1000 Megahertz. For example a modified amplifier is connected to an output tank coil which is in a parallel resonant circuit (also commonly called a pi circuit) which, when tuned to resonance has a very high impedance and consequently high voltage across it. If the electrode is very fine the voltage moves to the end of the electrode. This high, potential energy had no place to go other than out at the end point of a wire or attached fine rod which projects into the atmosphere. This energy, as it rushed out at the small end point of the rod, causes the rod to get red hot and emit an arc like discharge.

A new unique method of the use of such a basic metallic discharger has now been discovered. It was discovered that the characteristic of the metallic discharger could be used as a way of making particles which can cause welding or coating because they posses both heat and kinetic energy in the discharge.

An exemplary apparatus 100 which can be used to produce antimicrobial coatings and surfaces in accordance with exemplary embodiments of the present invention is shown in FIG. 1. Such exemplary apparatus 100 can be configured to produce an electrical arc or discharge 8 at a distal end of an electrode 2, where the arc or discharge 8 can be produced without the distal end of the electrode 2 being in proximity to an electrically grounded object.

For example, the exemplary apparatus 100 can be based on a one-sided electrode arrangement which may be configured to deposit particles on a substrate or other surface. These deposits are not resins which can be washed off but are firmly adherent and possibly fused small size particles. This exemplary technique may provide small particles which can be fused to the surface. For example, it is anticipated that silver particles may be welded to a surface by the one sided electrode method for antibacterial use. Such exemplary apparatus 100 can include, e.g., a high-frequency electrical generator or power source 1, a conductive coil 3 which may be provided as a coiled tube, and can be formed, e.g., using copper or another conductive material, and an electrode 2 which can be formed of or include a material to be deposited as at least part of an antimicrobial material or coating. The electrode 2 may be conductive or semiconductive. Capacitors 4, 5, 6 can be provided in an electrical communication with the conductive coil 3, which may exhibit electrically inductive properties. For example, capacitors 4, 5, 6 and coil 3 may together form a conventional Pi circuit, or exhibit electrical behavior similar to such circuit. A carrier gas 7 may also be provided adjacent to the electrode 2.

When the exemplary apparatus 100 is operated, an electrical arc or discharge 8 may be produced near a distal end of the electrode 2, and ionic particles 9 may be emitted from the electrode 2. Such particles can be expelled onto a nearby substrate and may adhere to such substrate, forming a strong mechanical bond. The an electrical arc or discharge 8 can be produced from the distal end of the electrode 2 using such exemplary one-sided electrode apparatus 100, even if the distal end of the electrode 2 is not proximate to an electrically grounded object. Thus, the an electrical arc or discharge 8 may be produced in proximity to electrically nonconductive substrates, in contrast to conventional arc welding systems and the like.

Figure 2:
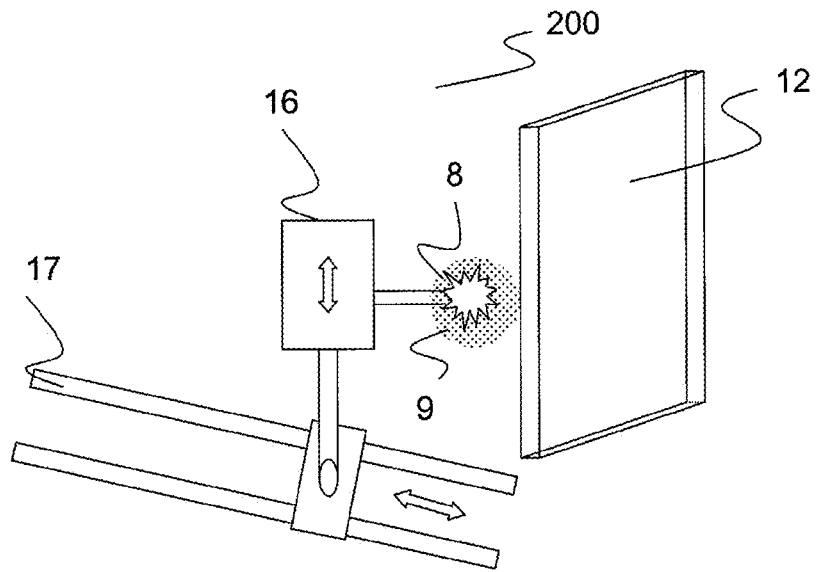
FIG. 2 is an illustration of the exemplary apparatus which may be used to produce antimicrobial coatings on large substrates in accordance with other exemplary embodiments of the present invention.

A further exemplary apparatus 200 is shown in FIG. 2 which can be used to provide an antimicrobial coating on a large substrate 12. Such exemplary apparatus 200 can include a deposition arrangement 16, which may be configured to produce an electrical arc or discharge 8 and emit ionic or other particles 9. The deposition arrangement 16 can be affixed to a translating arrangement 17, which can controllably move the deposition arrangement 16, e.g., along or over at least a portion of a large substrate 12. Thus, particles 9 can be deposited on a large substrate to form an antimicrobial coating thereon. The translating arrangement 17 can include or communicate with a controller (not shown) which can control the position and/or speed of the deposition arrangement 16 relative to the substrate 12. Thus, the location and amount of deposited coating formed by the particles 9 can be controlled. For example, such controller can control a position of the distal end of the electrode 8 relative to the substrate 12, e.g., provide a substantially constant distance between them, which can further allow a more uniform deposition of particles 9 on the substrate 12.

Figure 3:
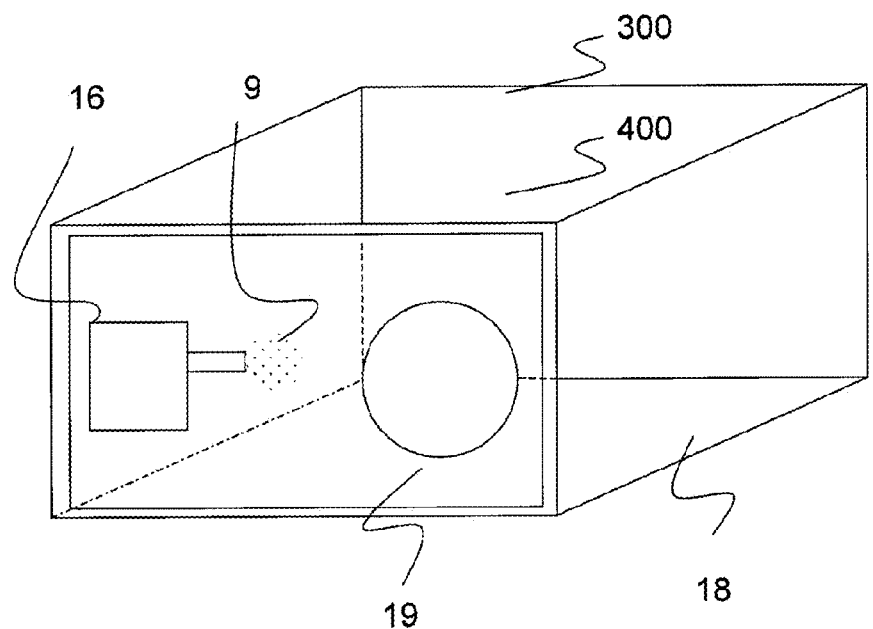
FIG. 3 is an illustration of the exemplary apparatus which may be used to produce antimicrobial coatings in accordance with further exemplary embodiments of the present invention.

A still further exemplary apparatus 300 which can be used to provide an antimicrobial coating is shown in FIG. 3. Such exemplary apparatus 300 can include the deposition arrangement 16, which (as described above) may be configured to emit particles 9. The deposition arrangement 16 can be provided at least partially inside an enclosure 18, and the enclosure 18 can further enclose an object 19 to be coated with an antimicrobial coating. Using this exemplary apparatus 300, the particles 9 can be deposited on an object 19 to form an antimicrobial coating thereon. Further, any of the particles 9 which are not deposited on the object 19 may remain in the enclosure 18. This exemplary configuration can assist in recovering such particle material, which may be then be reused or recycled.

Figure 4:
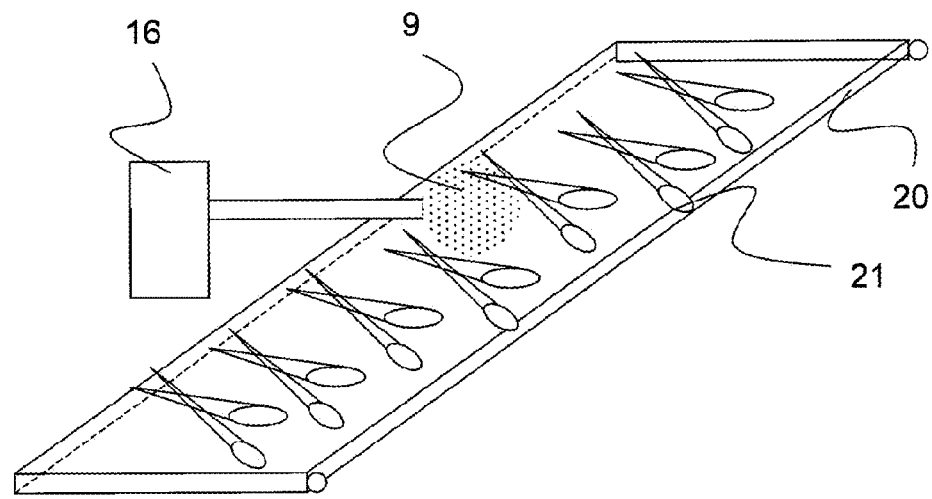
FIG. 4 is an illustration of the exemplary apparatus which may be used to produce antimicrobial coatings in accordance with additional exemplary embodiments of the present invention.

Yet another exemplary apparatus 400 which can be used to provide an antimicrobial coating is shown in FIG. 4. Such exemplary apparatus 400 can again include the deposition arrangement 16, which is configured to emit the particles 9. The deposition arrangement 16 can be provided in proximity to a conveyor belt 20 or similar transport apparatus. A plurality of objects 21 to be coated with an antimicrobial coating can be provided on the conveyor belt 20. Using this exemplary apparatus 400, particles 9 can be continuously deposited on a large number of objects 21 to form an antimicrobial coating thereon. System parameters, such as speed of the conveyor belt 20 and intensity of discharged particles 9, may be adjusted to provide a suitable amount or thickness of the coating on the objects 21.

In further exemplary embodiments of the present invention, the electrode 2 can have a form of a wire that may be continuously fed as it is consumed to form particles. A control arrangement can be provided which includes, e.g., a feedback arrangement to control the speed at which such wire is fed, and which can preferably maintain a substantially constant distance between the distal end of such wire electrode 2 and the substrate being coated. Such control arrangement can be based, e.g., on mechanical, optical, electrical, or thermal sensors. The voltage provided by generator 1 and the diameter of the electrode 2 may also be controlled to provide desired particle sizes. For example, thinner electrodes and/or higher voltages may produce smaller particle sizes.

According to still further exemplary embodiments of the present invention, a plurality of electrodes 2 may be used, where different ones of the electrodes 2 may have different compositions and/or diameters to provide particular desired properties in the deposited coatings. Such electrodes 2 may be provided with electrical power to generate a discharge either simultaneously or sequentially as the distal ends of the electrodes 2 are moved over the substrate. Different electrical frequencies can be applied to the different electrodes 2, and distal ends of such electrodes may also be provided at different distances from the substrate being coated. Alternatively, a varying electrical frequency may be applied to a single electrode 2 to produce variations in particle sizes and/or other properties in deposited coatings. For example, coatings having a range of compositions, compositional gradients, and/or coatings with a plurality of layers can be created using a plurality of such electrodes 2.

In yet further exemplary embodiments of the present invention, a coating of antimicrobial material may be provided on a substrate using a single-sided electrode arrangement 100 similar to one shown in FIG. 1. The electrode 2 may have a form of a rod or wire, and can be electrically conductive or semiconductive. An antimicrobial material or coating may be produced by providing an ionized discharge 8 (e.g., an electrical arc) at a distal end of the electrode 2, and placing a substrate to be coated in proximity to the discharge 8. The discharge 8 may be continuous, and it can be formed in the absence of a nearby object that is electrically grounded. The particles 9 produced by an interaction between the discharge 8 and the material of the electrode 2 can impinge on the nearby substrate and adhere thereto.

The particles 9 which may be used to form the antimicrobial coating may have an average size that is less than about 1000 nm, less than about 800 nm, or preferably less than about 500 nm, or more preferably less than about 200 nm. The particles 9 may have a shape that is approximately, spherical, cylindrical, acicular, or a mixture of these geometries. The small particles 9 which can form the antimicrobial coating can be unsintered or only partially sintered, and may retain an open porous structure even at high temperatures. The particles 9 can also remain adherent to the substrate and may resist further densification and pore closure at high temperatures (e.g., about half of the absolute melting temperature of the substrate or a constituent thereof). The antimicrobial coating may further be resistant to wear or removal from the substrate under a range of conditions, e.g., rubbed or abraded against other objects, washed or otherwise cleaned, exposed to chemicals and solvents, etc. The surface area density of the surface coated with small particles may be approximately 3 or 4.

The electrode 2 may be used to generate particles 9, which may then form at least a portion of the antimicrobial materials. Such electrode 2 can include, e.g., silver, copper, titanium, chromium, aluminum or a mixture of iron silicate, silicon nitride, alumina, silicon carbide, silica (e.g., any oxide of silicon), silicon, chromium and carbon. For example, deposition of particles 9 may produce combinations and/or mixtures of the above-mentioned elements and/or compounds during deposition on a substrate. Such compounds and mixtures may include further compounds which can result from reactions of the particles 9 with, e.g., moisture, oxygen and/or nitrogen from surrounding air or deliberately introduced gases during deposition. For example, particles containing oxycarbonitrides could be formed and deposited on the substrate.

Figure 5:
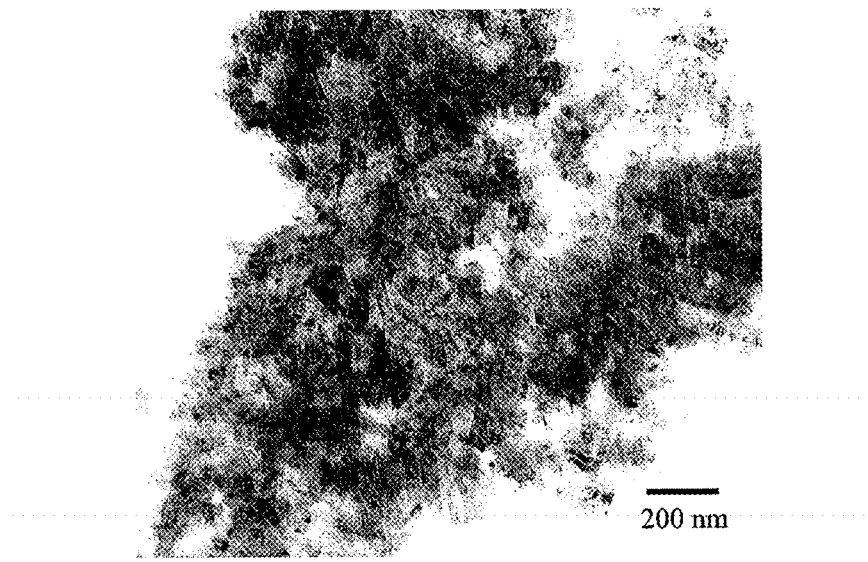
FIG. 5 is an exemplary image of an exemplary antimicrobial coating provided by a transmission electron microscope ("TEM") in accordance with certain exemplary embodiments of the present invention.
Figure 6:
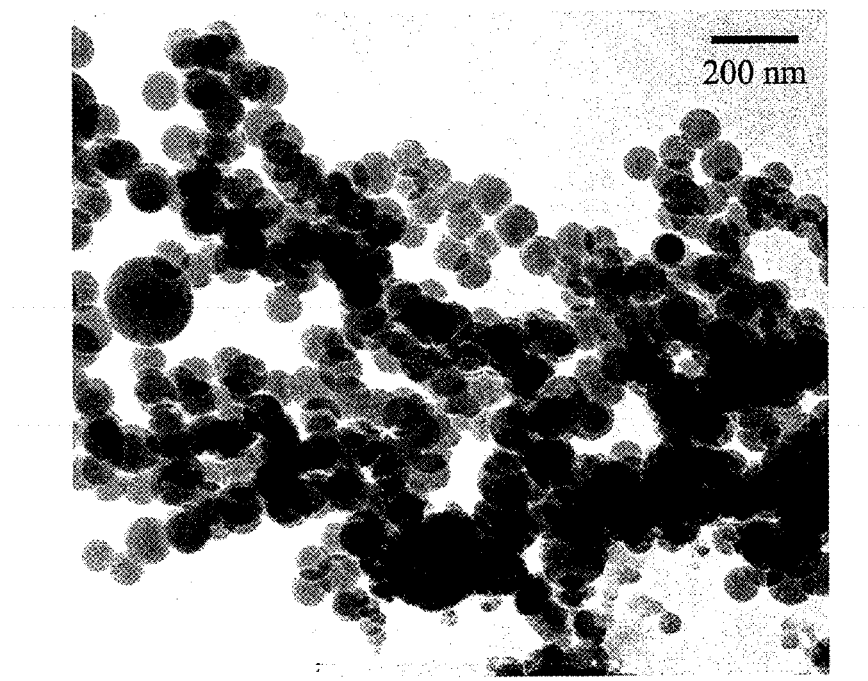
FIG. 6 is another exemplary image TEM image of a further exemplary antimicrobial coating in accordance with further exemplary embodiments of the present invention.
Figure 7:
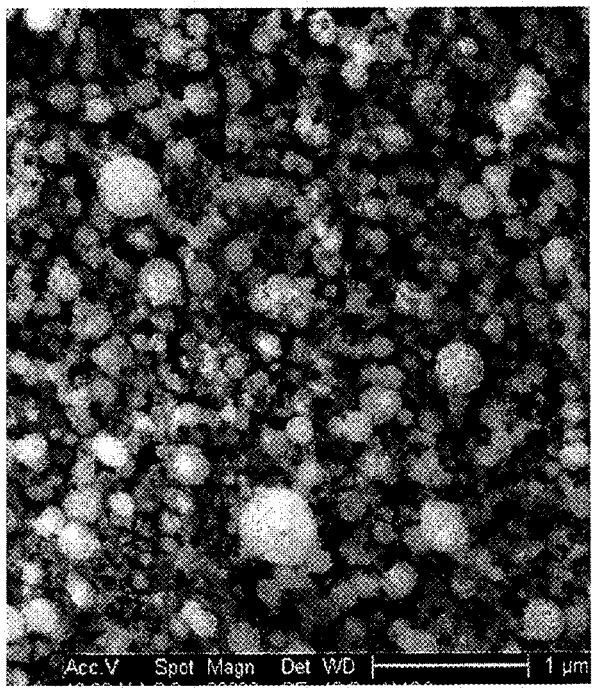
FIG. 7 is an exemplary image of an exemplary antimicrobial coating composed of particles provided by a scanning electron microscope ("SEM") in accordance with certain exemplary embodiments of the present invention. Note that the size of particles could range from highly sub micron ($10^{-3}$ microns) to several micrometers.
Figure 8:
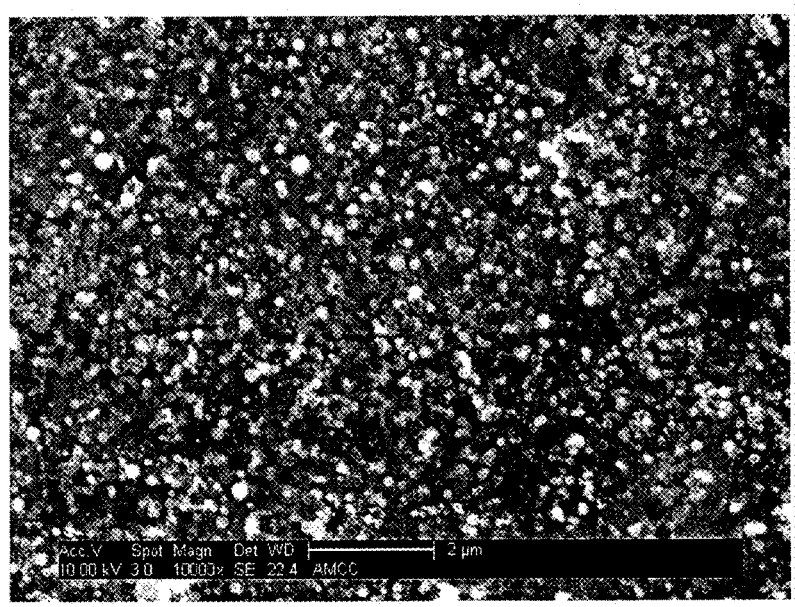
FIG. 8 is another exemplary SEM image of a further exemplary antimicrobial coating in accordance with further exemplary embodiments of the present invention.

Magnified views of exemplary antimicrobial coatings deposited on substrates in accordance with exemplary embodiments of the present invention are shown in FIGS. 5-8. For example, FIG. 5 shows an exemplary transmission electron microscope ("TEM") image of a material containing carbon nanoparticles. An exemplary TEM image of silica nanoscale particles which were deposited on a stainless steel substrate in accordance with exemplary embodiments of the present invention is shown in FIG. 6. FIG. 7 is an exemplary scanning electron microscope ("SEM") image of small particles containing aluminum which were deposited on a stainless steel substrate. Such particles have been observed to be strongly adherent to the substrate, and did not rub off even when applying mechanical erosion techniques. FIG. 8 is an exemplary SEM image of copper-based particles which were deposited on a stainless steel substrate.

The small particles, which may be microscopic or nanoscale (e.g., having an average size that is less than about one micron), can be deposited as one or more layers on a substrate. Preferably, such deposited particles will not be in a substantially sintered condition, e.g., they may still exhibit a degree of porosity after being deposited on a substrate.

Antimicrobial materials and coatings as described herein can be durable because the morphology of the deposited particles (e.g., their approximate size, degree of porosity or interconnectedness, etc.) may be essentially retained during exposure to high temperatures, mechanical forces, chemicals, etc. A high specific surface area may persist in such particulate antimicrobial coatings and materials, even if some amount of oxide or other reactive compound may form thereon, because of the presence of the initial microscopic or nanoscale particles, which can influence the growth rate of such compounds at least in the initial stages of growth.

Exemplary durable antimicrobial materials in accordance with exemplary embodiments of the present invention can be created using the exemplary apparatus shown in FIG. 1. For example, a commercial generator 1 may be used which provides alternating current at approximately 14 MHz from a 208 volt, 3 phase input. Such generator 1 can be can be provided in electrical contact with one side of a conventional Pi circuit (e.g., inductive coil 3 and capacitors 4, 5, 6). For example, the coil 3 may have a diameter of several inches (e.g., between about 2 inches and 6 inches), and the capacitors 4, 5, 6 can have a capacitance value of between about 30 picofarads and about 100 picofarads. The Pi circuit may include such components (e.g., coil 3 and capacitors 4, 5, 6) which may have values that lie outside these approximate ranges. The other side of the Pi circuit can be provided in electrical contact with one or more electrodes 2. Such electrodes 2 can be, e.g., wires which contain one or more particular compositions that can be used to form the exemplary antimicrobial coatings described herein.

When the generator 1 is powered, the distal end of the electrode 2 may be provided a few inches away from the substrate to be coated. For example, a distance of a between about 1 inch and about 6 inches can be used, or preferably a distance of about 3-4 inches. Other distances may be used depending on the amount of power supplied, the diameter and material of the electrode, etc. The distal end of the electrode can be passed over a portion of the substrate to cover a particular area thereof with the exemplary antimicrobial coating. A substrate exposure time of several seconds (e.g., about 1-10 seconds) may be sufficient to form such exemplary coating on the substrate. The exposure time can represent, e.g., a duration of time in which power is provided to emit particles from an electrode that is stationary relative to a substrate, or a duration of time in which particles from an electrode are provided onto a particular portion of a substrate, where the electrode and substrate are in relative motion to each other. Such residence time can be increased, e.g., by providing multiple passes of an electrode over a particular portion of a substrate. Such multiple passes using at least two different electrodes on different passes (or using one electrode supplied with electrical energy having different characteristics such as, e.g., frequency for different passes) may be used to create multilayered coatings which can include a plurality of layers having different compositions, particle sizes, or other properties.

The particles formed from the electrode, which may be deposited on the substrate to form an antimicrobial coating, may preferably have a size on the order of a few hundred nanometers or less. For example, the average particle size may be less than about 1000 nm, less than about 800 nm, preferably less than about 500 nm, or more preferably less than about 200 nm. Smaller electrode diameters may be used to form smaller particles. For example, an electrode having a diameter of about 1 mm or less can be used to form particles having a size of a few hundred nm or less. Several such thin electrodes may be provided in proximity to each other to cover a larger area of a substrate more quickly and/or uniformly.

The coating formed on the substrate can be very thin, e.g., on the order of several particle layers or less. Thinner coatings may be preferable, e.g., with respect to cost, durability, antimicrobial properties, formation time, etc. For example, exemplary antimicrobial coatings can have a thickness that is less than about 2000 nm, or preferably less than about 1000 nm. In certain exemplary embodiments of the present invention, the coating thickness can be less than about 800 nm, or less than about 500 nm, or even less than about 250 nm. The exemplary particle and coating dimensions described herein can provide coatings which may be very durable and firmly adherent to the substrate. Such exemplary coatings and materials as described herein were surprisingly found to exhibit antimicrobial properties.

Metals which may be used to form antimicrobial materials in accordance with exemplary embodiments of the present invention can exhibit an efficacy which may be related to their placement in a standard electromotive force ("EMF") series (e.g., a galvanic series) such as that shown in Table 1. For example, as suggested by the results shown in Table 2A and FIGS. 11-14 herein, antimicrobial efficacy of a metal may improve with a higher placement in the EMF series, e.g., metals that are more cathodic (having a more positive EMF with respect to a standard hydrogen electrode) may be more effective in killing or preventing growth of microbes. Thus, one or more such cathodic metals may preferably be used to form electrodes and resultant particles therefrom, which can in turn be used to form antimicrobial materials and coatings as described herein. Such metals may be selected for particular applications based on such factors as, e.g., cost and efficacy.

For examples, electrodes may be used which include noble metals such as, e.g., Cu, Ag, Au, Pt, Pd, or Ir. Such noble metals may provide particularly effective antimicrobial properties. Other elements which may also be used include, e.g., Ti, Si, Al, Sn, Sb, Sr, Ni, Be, U, Co, Se, Mg, Mo, V, Mn, Fe, W, Mo, Os, Hf, La, Ta, Cd, Nb, B, Si, Ge, As, Sb, Te, or Po. Rare earth metals may also be used, as well as compounds of rare earth metals such as, e.g., lathanum chromate, lanthanum chromite, strontium-doped lanthanum chromite, lanthanum oxide, $CeO_2$, ceriumoxychloride, or mischmetal. Electrodes which comprise transition metals, silver, tungsten, iron, SiC, $SiO_2$, or an oxide of nickel, iron, tungsten, or chromium may be preferable.

Further materials which may be used to form electrodes and particles therefrom to provide antimicrobial coatings can include, e.g., oxides, carbides, or halides of metal such as Cu, Ag, Au, Pt, Pd, or Ir. Coatings and materials in accordance with exemplary embodiments of the present invention may also be provided using particles which include semiconductors or semiconducting compounds such as, e.g., Si, Ge, As, SiC, or GaAs. Oxides and other compounds such as iron oxide, tungsten oxide, chromium oxide, zinc oxides, tin oxides, iridium oxides, $V_2O_5$, $Fe_2O_3$, $Fe_3O_4$, NiO, $MnO_2$, $SiO_2$, $MoO_3$, $HfO_2$, $WO_3$, $TiB_2$, $CrO_3$, $Nb_2O_5$, $Al_2Zr$, $B_4C$, $SiO_2$, ZrSiO4, $B_2O_3$, CdS, MnS, $MoS_2$, $NaN_3$, NaCN, $Si_2N_4$, PbO, $PbO_2$, $WO_2$, $BaO_2$, or mixtures and combinations thereof may also be used to form exemplary antimicrobial coatings and materials. Defect compounds, or nonstoichiometric compounds, may also be used such as, e.g., $SiO_x$, $NiFe_yO_x$, $MoS_x$, $Fe_zNO_x$, or other such compounds, where x, y, and z can represent non-integer values. Such defect compounds may exhibit particularly desirable antimicrobial properties.

Coatings and materials in accordance with certain exemplary embodiments of the present invention may also be provided using particles which include silicon carbide, siliconoxycarbide, siliconoxynitrocarbide, ironsilicate, molybdenumcarbosilicide, or other carbides, as well as phosphides, sulfides, silicides, or combinations thereof. Conductive nom-metals may also be used including, e.g., tin oxide, zinc oxide, iridium oxide, ruthenium oxide, a nickel ferrite, or yittrium-doped zirconia.

For example, a combination of particles may be selected which can be formed as compounds including, e.g., $SiO_2$, SiC, $MoSi_2$, or mixtures thereof. Carbon nanoparticles may also be used in exemplary embodiments of the present invention. Such nanoparticles can include, e.g., carbon nanotubes, carbon particles having other morphologies, or mixtures thereof.

TABLE 1

Standard EMF Series for Certain Metals

| Type | Metal-metal ion equilibrium | Electrode potential with respect to standard hydrogen electrode at 25° C. (volts) |
|---|---|---|
| Noble or cathodic | Au—$Au^{+3}$ | +1.498 |
|  | Pt—$Pt^{+2}$ | +1.2 |
|  | Pd—$Pd^{+2}$ | +0.987 |
|  | Ag—$Ag^{+1}$ | +0.799 |
|  | Hg—$Hg_3^{+2}$ | +0.788 |
|  | Cu—$Cu^{+2}$ | +0.337 |
| Neutral | $H_2$—$H^+$ | 0.000 |
|  | Pb—$Pb^{+2}$ | −0.126 |
|  | Sn—$Sn^{+2}$ | −0.136 |
|  | Ni—$Ni^{+2}$ | −0.250 |
|  | Co—$Co^{+2}$ | −0.277 |
|  | Cd—$Cd^{+2}$ | −0.403 |
|  | Fe—$Fe^{+2}$ | −0.440 |
|  | Cr—$Cr^{+2}$ | −0.744 |
|  | Zn—$Zn^{+2}$ | −0.763 |
|  | Al—$Al^{+3}$ | −1.662 |
|  | Mg—$Mg^{+2}$ | −2.363 |
|  | Na—$Na^{+1}$ | −2.714 |
| Active or anodic | K—$K^{+1}$ | −2.925 |

Source: A. J. deBethune and N. A. S. Loud, "Standard Aqueous Electrode Potentials and Temperature Coefficients at 25° C.," Clifford A. Hampel, Skokie, 1964.

Exemplary coatings which include nonconductive materials may be formed in several ways. For example, a nonconductive thin rod or fiber may be covered with a conductive material to provide such electrode. In one exemplary embodiment, a silica fiber provided with a metallic coating (e.g., silver, tungsten, or iron) may be used as an exemplary electrode. Alternatively, one or more nonconductive rods or fibers may be provided adjacent to one or more conductive rods or fibers. A discharge formed at the distal end of a conductive rod or fiber as described herein can produce particles of both the conductive and nonconductive materials, which may then be deposited together on a substrate to form a coating in accordance with certain exemplary embodiments of the present invention. Electrical conductivity of such materials may change when deposited. For example, conductive oxide electrodes may gain oxygen during deposition and become non-conducting after being deposited. In certain exemplary embodiments of the present invention, a plurality of layers may be sequentially deposited using electrodes having different compositions, where certain layers may be conductive and others may be nonconductive. In this manner, antimicrobial coatings or materials exhibiting a variety of dielectric properties can be provided.

Two or more layers of particles may also be deposited on a substrate to form a coating containing particles of more than one composition. For example, a first deposition may be applied to a substrate using a first electrode having a first composition, and a second deposition may then be applied to the substrate using a second electrode having a second composition. This procedure can be further repeated if desired. In this exemplary manner, an antimicrobial coating containing particles having different compositions may be provided.

The compositions used and combinations thereof may be selected, e.g., based on antimicrobial properties, durability, cost, etc. For example, coatings containing nanoscale silver particles may have particularly effective antimicrobial properties. Antimicrobial coatings containing silver together with other compositions (e.g., oxides and/or other metals) may be provided which can be both cost effective and exhibit strong antimicrobial behavior. Particles containing silver can be deposited simultaneously or sequentially with particles having other compositions. Some antimicrobial particles may provide enhanced wear, an altered surface potential, or lubricating properties in addition to or in combination with strongly antimicrobial properties.

Exemplary antimicrobial coatings may not have the same composition as the initial starting material of the electrode(s) used to form them. For example, non-stoichiometric particles and other compounds may be produced during formation of such exemplary coatings by reaction of the starting materials with each other and/or with ambient substances such as, e.g., oxygen, nitrogen, carbon-containing gases, or moisture.

A combination of metallic and oxide particles may further be used as an antimicrobial coating such as, e.g., a coating containing W and $WO_3$. An oxide which forms in such exemplary coatings may be dispersed as separate particles within the coating. Alternatively, a surface of certain particles may oxidize while the interior of such particles may remain metallic. The oxide formed can be porous or non porous. Such oxides may be intentionally formed or enhanced, e.g., by exposing metal-containing coatings to an oxidizing atmosphere after they are deposited, optionally with simultaneous heating of the coatings. Such oxidation may also occur spontaneously in such coatings, e.g., during use. Alternatively, deposited coatings may be subjected to a reducing treatment after they are deposited on a substrate.

Exemplary antimicrobial coatings in accordance with exemplary embodiments of the present invention can provide additional wear resistance and/or durability to the substrate on which they are applied. Such exemplary coatings can be very thin, as described herein, and may not affect the performance of the coated object.

Exemplary embodiments of the present invention may be used to coat various objects with antimicrobial coatings in situ. For example, the exemplary apparatus described herein and shown, e.g., in FIG. 1, may not require any electrical grounding of the substrate. Thus, exemplary antimicrobial coatings may be applied to a variety of objects, including nonconductive objects, without relocation or removal of the object. For example, common objects such as faucet handles, doorknobs, etc., may be coated simply by providing an electrode having a discharge as described herein in proximity to the object. If the antimicrobial properties of a coated object somehow diminish over time, they can be 'rejuvenated' by reapplying a coating of the antimicrobial material as described herein.

Examples

Antimicrobial tests were performed on a number of exemplary substrates in accordance with exemplary embodiments of the present invention, under a range of conditions. In certain exemplary tests, a layer of silver particles having a size of approximately 100 nm was deposited on a stainless steel substrate using the exemplary apparatus described herein. Bacterial cultures were then introduced onto the coated substrate (e.g., at a density of approximately $10^5$ bacteria per square cm.). After certain treatment times elapsed (which were about 2 hours or longer), the presence of residual bacteria was measured using AOAC method 988.18 in sterile Petri dishes. In this standard testing technique, a material is swabbed with a sterile cotton swab and the swab is introduced into a nutrient in the Petri dish. The Petri dish is then shielded from light and maintained at a temperature of about 32° C. Bacterial colonies, if any appear, may become visible after about 20 hours. A kit used to perform such bacterial tests was obtained from Micrology labs (based in Indiana). The presence and growth of bacteria colonies in such tests can be catalyzed, e.g., by nutrients in the Petri dish. Addition of a tetrazine salt to the Petri dishes (which may be provided, e.g., in the nutrients directly or during manufacture or preparation of the dish) can cause the bacteria colonies to appear red in color, which may aid in their identification.

Figures 9A, 9B:
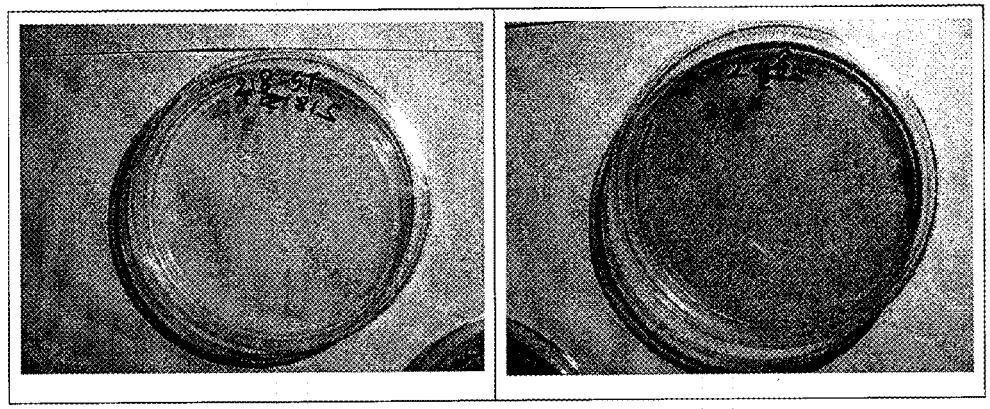
FIG. 9A is an exemplary illustration of a bacterial culture dish exhibiting no bacterial colonies.
FIG. 9B is an exemplary illustration of a bacterial culture dish exhibiting a large number of bacterial colonies.

For example, such antimicrobial test was performed on a substrate which was coated with a layer of silver particles in accordance with exemplary embodiments of the present invention. The coating was inoculated with *Enterobacter Aerogenes* bacteria as described herein. A clean Petri dish, which can indicate substantially complete elimination of bacterial colonies by such antimicrobial coating, is shown in FIG. 9A. The same substrate which was not provided with such antimicrobial coating was also tested under similar conditions. The test results for the uncoated substrate, shown in FIG. 9B, reveal a substantial number of bacterial colonies. The darker shading in FIG. 9B as compared with FIG. 9A indicate presence of such colonies on a fine scale. In these tests, an antimicrobial coating containing silver particles was observed to provide substantially complete elimination of the bacteria.

Various antimicrobial materials, test conditions, and observations (e.g., bacterial colony counts) are shown in Table 2A and FIGS. 11-14. In these tables (and in Table 3A and FIGS. 15-17), experiment numbers containing "xT" indicates x number of passes were made with an electrode over a substrate to form the coating, experiment numbers containing "yH" indicates that samples were collected from the same surface after y hours (to determine longevity of the antimicrobial behavior), and times are given in the format of Hours: Minutes."

Bacteria used in these exemplary tests include *Enterobacter Aerogenes* bacteria and *Bacillus Cereus* bacteria. The results shown in Table 2A and FIGS. 11-14 reveal the unexpected observation that a wide range of coatings as described herein can exhibit significant antimicrobial properties and an anti-bacterial surface resistant to chemical, electrochemical and mechanical attack as far as the efficacy of the surface to killing bacteria is concerned.

The antimicrobial materials and coatings in accordance with exemplary embodiments of the present invention can be differentiated from resins or other chemically-applied coatings, which may be washed off, scraped off, or otherwise easily removed from a substrate. Instead, exemplary coatings in accordance with exemplary embodiments of the present invention can be formed of very small particles that are firmly adherent to a substrate and to each other. Such coatings may not require further heat treatment (e.g., sintering treatment) after being applied to a substrate. The exemplary antimicrobial coatings described herein were not removed from the substrates even after the surface was vigorously abraded.

Table 3A and FIGS. 15-17 show further tests performed on exemplary antimicrobial coatings formed using a range of particles, including Cu, Al, Ag, Ti, W, $WO_3$, oxides of metals, mixed oxides, Fe, Ni, certain carbides, oxycarbides, nonstoichiometric compounds, nitrides, oxynitrides, and mixtures thereof. These data suggest that coatings formed using compositions having a higher EMF relative to a standard hydrogen electrode (e.g., more cathodic compositions, such as noble metals) may often exhibit improved antimicrobial properties. The data in these tables further suggest that coatings containing oxide particles may be more effective than those with no oxides in killing or inhibiting growth of microbes. Coatings formed using particles containing, e.g., carbides, nitrides, oxycarbides, fluorides, nitrides, and/or combinations thereof may also exhibit favorable anti microbial properties. Such antimicrobial surfaces described herein may, for example, provide such effects as inactivating certain enzymes, altering certain nucleic acids and/or cytoplasmic membranes, affecting local pH values or driving forces for energy molecules within cells, etc. Such effects may kill or inhibit growth of certain microorganisms.

Further exemplary antimicrobial coatings were formed by depositing different materials, including silver, carbon, silicon carbide, aluminum, copper, tungsten, iron, nickel, and titanium, on stainless steel substrates using the exemplary techniques described herein. Five passes of the distal end of an electrode producing a discharge and particles were made over the substrate to form each coating.

*Enterobacter aerogenes* bacteria suspended in liquid media were swabbed onto surfaces of the coated stainless steel substrates and also on an uncoated stainless steel substrate for comparison. The bacteria was allowed to remain on the surfaces for about 2 hours.

Figure 10:
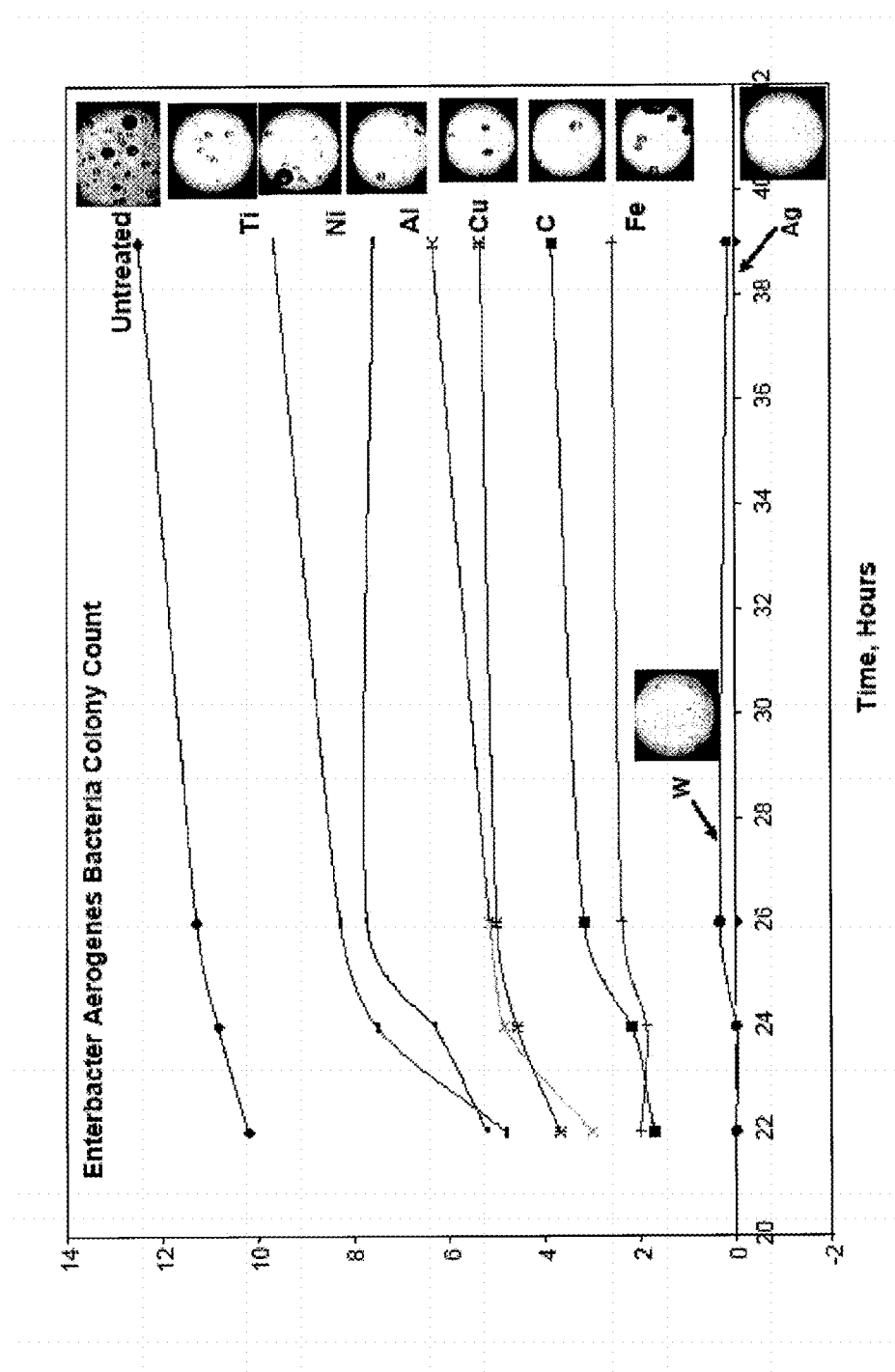
FIG. 10 is an exemplary graph of observed antimicrobial behavior for stainless steel substrates coated with exemplary coatings containing a variety of materials in accordance with exemplary embodiments of the present invention.

Using an AOAC test procedure 988.18 and/or 989.11 as described herein, a bacteria count for the *Enterobacter Aerogenes* bacteria was made for each surface tested. The bacteria colonies were counted using a polarized microscope at various time intervals, including 22, 24, 26, and 39 hours. The number of bacteria colonies were counted using a light microscope at 40× magnification. The number of colonies observed in a field of view of the image was recorded for each tested surface. Six different locations of each Petri dish were used to obtain such colony counts. An average of the colony counts was determined at each time interval. A graph containing the results of this analysis is shown in FIG. 10. Images of the observed bacterial colonies corresponding to 24 hours of incubation time are also shown in the FIG. 10.

These results suggest that exemplary coatings made using silver particles exhibit particularly strong antimicrobial properties. Such coatings containing tungsten (W), iron (Fe), and carbon particles were observed to be effective at inhibiting the growth and/or spreading of the *Enterobacter Aerogenes* bacteria. Exemplary coatings containing copper (Cu), aluminum (Al), nickel (Ni) and titanium (Ti) were observed to exhibit somewhat less effective antimicrobial behavior. Nevertheless all such exemplary coatings in accordance with exemplary embodiments of the present invention were observed to exhibit better antimicrobial properties than an uncoated stainless steel substrate.

Further exemplary antimicrobial coatings have been produced which include various combinations of SiC, $SiO_2$, and oxides of nickel, iron and chromium. Such components may form non-stoichiometric compounds in the exemplary antimicrobial coatings (e.g., the oxides may have a high defect concentration when formed as particles and deposited on a substrate as described herein). Testing these exemplary coatings for antimicrobial properties as described herein revealed that they generally produced very small counts of bacterial colonies, e.g., counts which were less than about 2 after 24 hours of incubation time. For example, such materials exhibited antimicrobial behavior which was at east as good as that of iron (Fe) as shown in FIG. 10. Exemplary coatings in accordance with exemplary embodiments of the present invention were also produced using, e.g., coated optical fibers as electrodes, and were also observed to exhibit excellent antimicrobial properties.

Exemplary embodiments of the present invention can provide a wide range of objects having antimicrobial properties. Such objects can include, e.g., biological implants (e.g., bone screws, stents, artificial joints such as replacement knee joints, hip joints, or components thereof), medical instruments (e.g. needles, scalpels and other blades, thermometer probes, etc.), health aids such as, e.g., hearing aids or eyeglasses, kitchen utensils (e.g., knives, scissors, flatware, pots and pans, food processor or mixer blades, etc.). Objects which can be provided with antimicrobial coatings in accordance with exemplary embodiments of the present invention can further include faucets, doorknobs, handles, toilets and urinals, sinks, and other such objects which people may commonly come into contact with.

For example, cosmetic articles such as rings, bracelets, necklaces, and other jewelry can be provided with antimicrobial coatings in accordance with exemplary embodiments of the present invention. Certain components may be included in such coatings, if desired, to improve an aesthetic appearance of these articles. Industrial articles and tools such as, e.g., screw drivers, wrenches, etc. can also be provided with antimicrobial coatings. Industrial surfaces which may accumulate dirt and/or microbes during use, including those which may retain substances such as oil films or water can also be provided with antimicrobial coatings in accordance with exemplary embodiments of the present invention. In a previous application we have noted that nano particle covered surfaces (not sintered but small particles held in place by welding tend to retain water films without allowing the water to evaporate easily (see PCT/US06/60621 filed in the US on Nov. 7, 2006). For example, surfaces in "clean rooms" which may be used for semiconductor processing or to provide sanitary medical environments can also be provided with antimicrobial coatings as described herein.

Further, there may be a need for controlling soil bacteria and to promote healthy plant growth by providing antibacterial or antimicrobial surfaces around plants, e.g., household plants, plants grown in nurseries, and for other general agricultural applications. Exemplary embodiments of the present invention can provide such surfaces, e.g., for planting pots, hydroponic equipment, etc., and may allow a reduced dependency on fungicides and/or pesticides. For example, a microbial selection or isolation can be achieved using antimicrobial structures and compounds, where changes in concentrations of specific microbes can be controlled using exemplary embodiments of the present invention.

In further exemplary embodiments of the present invention, rough or defective surfaces or objects may be treated by filling cracks, crevices and/or pores with antimicrobial materials using the exemplary method and apparatus described herein. Alternatively, antimicrobial materials may be provided using the exemplary apparatus, method, and compositions described herein,

Having thus described in detail preferred embodiments of the present invention, it is to be understood that the invention defined by the appended claims is not to be limited to particular details set forth in the above description, as many apparent variations thereof are possible which lie within the scope of the present invention as recited in the appended claims. Certain modifications and variations of the method, apparatus, and compositions described herein will be obvious to those skilled in the art, and are intended to be encompassed by the following claims.

TABLE 2A

Microbial Test Results for Certain Coated and Uncoated Substrates

| Expt # | Substrate Material | Deposited Material (including wt gain after deposition, when measured) | Sample size, mm | Bacterium treatment (BT), minutes | Swab collection time and date | Temperature of Incubation, ° F. | # of colonies at specified hour of incubation. | # of colonies at specified hour of incubation |
|---|---|---|---|---|---|---|---|---|
| 207-5T | SS | Cu | 1 × 21 × 33 | 12 minutes in Soil water of 23 H old {Aug. 16, 2006 3:35 PM} | After 3:00 hours of BT. (Aug. 16, 2006- Aug. 18, 2006) | 90-95 | 47 colonies @ 22:32 {Aug. 17, 2006} | 58 colonies @ 49:00 {Aug. 18, 2006} |
| 211 | SS | No | 1 × 21 × 33 | 12 minutes in Soil water of 23 H old {Aug. 16, 2006 3:35 PM} | After 3:00 hours of BT. (Aug. 16, 2006- Aug. 18, 2006) | 90-95 | 61 colonies @ 22:23 {Aug. 17, 2006} | 81 colonies @ 49:00 {Aug. 18, 2006} |
| 213 | SS | No | 1 × 20 × 30 | 12 minutes in Soil water of 48 H old (Aug. 17, 2006} | After 0:52 Mts of BT. (Aug. 17, 2006) | 95 | 136 colonies + Fine dots@ 17:00 {Aug. 18, 2006} | |

TABLE 2A-continued

Microbial Test Results for Certain Coated and Uncoated Substrates

| Expt # | Sub-strate Material | Deposited Material (including wt gain after deposition, when measured) | Sample size, mm | Bacterium treatment (BT), minutes | Swab collection time and date | Temperature of Incubation, °F. | # of colonies at specified hour of incubation. | # of colonies at specified hour of incubation |
|---|---|---|---|---|---|---|---|---|
| 208-5T | SS | Al (Light blue color) | 1 × 21 × 33 | 12 minutes in soil water of 68 H old {Aug. 18, 2006 12:20 PM} | After 68:00 hours of BT. (Aug. 21, 2006) 8:30 AM | 90 | | |
| 214 | SS | No | 1 × 21 × 33 | 12 minutes in soil water of 68 H old {Aug. 18, 2006 12:20 PM} | After 68:00 Hours of BT. (Aug. 21, 2006) 8:30 AM | 92 | | |
| 209-5T | SS | SiC | 1 × 21 × 33 | 12 minutes in soil water of 71:15 (Hours:Mins) old solution {Aug. 18, 2006 3:35 PM} | After 64:30 Hours:Mins of BT. (Aug. 21, 2006) 8:30 AM | 92 | | |
| 210-2T | SS | Cu | 1 × 21 × 33 | 12 minutes in soil water of 71:15 (Hours:mins) old {Aug. 18, 2006 3:35 PM} | After 64:30 Hours:Mins of BT. (Aug. 21, 2006) 8:30 AM | 92 | | |
| 215-5T | SS | C + 0.001 g Aug. 24, 2006 | 1 × 18 × 32 | Abandoned the coupon (accidentally fell down from table) | | | | |
| 216-5T | SS | C + 0.002 g Aug. 24, 2006 | 1 × 20 × 31 | *Enterobacter Aerogenes* Aug. 26, 2006 12:24 PM | After 24 hours of BT. (Aug. 27, 2006 12:20 PM) | 92 | None at 20 h:00 mts (Aug. 28, 2006 8:20 AM) | |
| 217-5T | SS | Ag + 0.012 g* Aug. 25, 2006 *nano & few micro deposition | 1 × 20 × 34 | *Enterobacter Aerogenes* Aug. 26, 2006 12:25 PM | After 24 hours of BT. (Aug. 27, 2006 12:22 PM) | 92 | None at 20 h:00 mts (Aug. 28, 2006 8:20 AM) | |
| 218-5T | SS | Ag + 0.021 g* Aug. 25, 2006 | 1 × 20 × 33 | *Enterobacter Aerogenes* Aug. 30, 2006 10:00 AM | After 2:03 (Hours:mins) of BT. Aug. 30, 2006 12:03 PM | 92 | None at 20:00 & 24:00 (Aug. 31, 2006 8:00 AM & 12:00 Noon) | |
| 219-5T | SS | SiC + 0.003 g Aug. 24, 2006 | 1 × 25 × 31 | *Enterobacter Aerogenes* Aug. 26, 2006 12:27 PM | After 24 hours of BT. (Aug. 27, 2006 12:24 PM) | 92 | None at 20 h:00 mts (Aug. 28, 2006 8:20 AM) | |
| 220-5T | SS | SiC + 0.003 g Aug. 24, 2006 | 1 × 22 × 31 | *Enterobacter Aerogenes* Aug. 30, 2006 10:00 AM | After 2:05 (Hours:mins) of BT. Aug. 30, 2006 12:05 PM | 92 | ~10% red dot over the entire PD at 20:00 & 24:00 Aug. 31, 2006 8:00 AM & 12:00 Noon | |
| 225 | SS | No | 1 × 25 30 | *Enterobacter Aerogenes* Aug. 26, 2006 | Aug. 26, 2006 SAT 11:30 AM | 92 | Dish full of red colored E-bacteria at 20:30 & 25:00 | Dish full of red colored E-bacteria at 44 h:40 mt |
| 226 | SS | No | 1 × 24 × 30 | *Bacillus cereus* | Aug. 26, 2006 SAT 11:30 AM | 92 | None at 25 h:00 mt on Aug. 27, 2006 | 11 red dots in entire Petri dish at 44 h:40 mt (Aug. 28, 2006 8:00 AM) |
| 226-R | SS | No | 1 × 24 × 31 | *Bacillus cereus* Aug. 27, 2006 12:27 pm | Swab collected after 41 minutes of BT (Aug. 27, 2006 SUN 1:08 PM) | 92 | None at 19 h:00 mt (Aug. 28, 2006 8:00 AM) | Large population of fine red dots at 25:00 Aug. 28, 2006 2:10 PM |

TABLE 2A-continued

Microbial Test Results for Certain Coated and Uncoated Substrates

| Expt # | Substrate Material | Deposited Material (including wt gain after deposition, when measured) | Sample size, mm | Bacterium treatment (BT), minutes | Swab collection time and date | Temperature of Incubation, ° F. | # of colonies at specified hour of incubation. | # of colonies at specified hour of incubation |
|---|---|---|---|---|---|---|---|---|
| 227 | SS | No | 1 × 21 × 31 | Enterobacter Aerogenes Aug. 28, 2006 10:35 AM | After 24 hours of BT. Aug. 29, 2006 Tue 10:35 AM | 92 (8/29) 88 (8/30 8:00 AM) 90 (8/30 10:00 AM) | None at 21:30 (Aug. 30, 2006 8:00 AM) | |
| 228 | SS | No | 1 × 21 × 31 | Enterobacter aerogenes Aug. 30, 2006 10:08 AM | After 2:00 (Hours:Mins) of BT. Aug. 30, 2006 12:08 PM | 92 | Dish full of red E-bacteria @ 20:00 & 24:00 Aug. 31, 2006 8:00 AM & 12:00 Noon | |
| 218-5T-2H-28H | SS | Ag | 1 × 20 × 33 | Enterobacter aerogenes Aug. 30, 2006 10:08 AM | (i) After 2:03 (Hours:Mins) on Aug. 30, 2006 12:03 PM, (ii) After 28:30 (Hours:Mins) on 8/31 at 4:30 PM | 92 | None at 15:00 & 25:00 on Sep. 1, 2006 at 8:00 AM & 6:00 PM | |
| 220-5T-2H-28H | SS | SiC Aug. 24, 2006 | 1 × 22 × 31 | Enterobacter Aerogenes Aug. 30, 2006 10:08 AM | (i) After 2:05 (Hours:Minutes) on Aug. 30, 2006 12:05 PM, (ii) After 28:30 (Hours:Mins) on 8/31 at 4:35 PM | 92 | None at 15:00 & 25:00 on Sep. 1, 2006 at 8:00 AM & 6:00 PM | |
| 228-2H-28H | SS | No | 1 × 21 × 31 | Enterobacter Aerogenes Aug. 30, 2006 10:08 AM | (i) After 2:05 (Hours:Mins) on Aug. 30, 2006 12:05 PM, (ii) After 28:30 (Hours:Mins) on Aug. 31, 2006 at 4:40 PM | 92 | None at 15:00 & 25:00 on Sep. 1, 2006 at 8:00 AM & 6:00 PM | |
| X243 | SS | No | 1× | Bacillus Cereus* Oct. 31, 2006 3:21 pm | Swab collected after 3:03 (Hours:Minutes) of BT on Oct. 31, 2006 6:24 PM | 90 85 | (i) None at 14:00 (Nov. 1, 2006 8:21 am), (ii) None at 24:00 (11/1; 6:30 pm) | (i) Very Fine red dots half of dishful bacteria at 37:30 (11/2; 8:00 am) |
| X244 | SS | No | 1× | Enterobacter Aerogenes Oct. 31, 2006 3:21 pm | Swab collected after 3:05 (Hours:Mins) of BT on Oct. 31, 2006 6:26 PM | 90 85 | None at 14:00 (on Nov. 1, 2006 8:21 am) | (i) Fine red dots dishful bacteria at 20:00 (11/1; 2:40 pm) |

TABLE 3A

Microbial Test Results for Certain Coated and Uncoated Substrates

| Expt # | Substrate Material | Deposited Material | Sample size, mm | Bacterium treatment (BT), minutes | Swab collected | Temperature of Incubation, ° F. | # of colonies at 15:00 & 20:00 hours of incubation. (MACRO Observation) | # of colonies at 22:00 hours of incubation. (MACRO Observation) |
|---|---|---|---|---|---|---|---|---|
| X235-5T | SS | Ag + 0.010 g | 1 × 22 × 29 mm | Enterobacter Aerogenes Nov. 20, 2006 2:14 PM | Swab collected after 3:00 (Hours:Mins) of BT on 11/20 5:14 PM | 78 F. (for first 16 h), 82 F. (16 h to 47 h) | None Nov. 21, 2006 8:20 AM & 1:30 PM | None Nov. 21, 2006 3:15 PM |

TABLE 3A-continued

Microbial Test Results for Certain Coated and Uncoated Substrates

| Expt # | Substrate Material | Deposited Material | Sample size, mm | Bacterium treatment (BT), minutes | Swab collected | Temperature of Incubation, °F. | # of colonies at 15:00 & 20:00 hours of incubation. (MACRO Observation) | # of colonies at 22:00 hours of incubation. (MACRO Observation) |
|---|---|---|---|---|---|---|---|---|
| X237-5T | SS | C No change in wt could be recorded because of the low sensitivity of the weigh scale | 1 × 20 × 31 mm | *Enterobacter Aerogenes* Nov. 20, 2006 2:15 PM | Swab collected after 3:00 (Hours:Mins) of BT on 11/20 5:15 PM | 78 F. (for first 16 h), 82 F. (16 h to 47 h) | None Nov. 21, 2006 8:20 AM & 1:30 PM | None Nov. 21, 2006 3:15 PM |
| X239-5T | SS | SiC + 0.003 g | | *Enterobacter Aerogenes* Nov. 20, 2006 2:16 PM | Swab collected after 3:00 (Hours:Mins) of BT on 11/20 5:16 PM | 78 F. (for first 16 h), 82 F. (16 h to 47 h) | None Nov. 21, 2006 8:20 AM & 1:30 PM | None Nov. 21, 2006 3:15 PM |
| X245-5T | SS | Al No change in wt could be recorded because of the low sensitivity of the weigh scale | 1 × 22 × 34 mm | *Enterobacter Aerogenes* Nov. 20, 2006 2:17 PM | Swab collected after 3:00 (Hours:Mins) of BT on 11/20 5:17 PM | 78 F. (for first 16 h), 82 F. (16 h to 47 h) | None Nov. 21, 2006 8:20 AM & 1:30 PM | None Nov. 21, 2006 3:15 PM |
| X247-5T | SS | Cu No change in wt. No change in wt could be recorded because of the low sensitivity of the weigh scale | 1 × 20 × 34 mm | *Enterobacter Aerogenes* Nov. 20, 2006 2:18 PM | Swab collected after 3:00 (hours:Mins) of BT on 11/20 5:18 PM | 78 F. (for first 16 h), 82 F. (16 h to 47 h) | None Nov. 21, 2006 8:20 AM & 1:30 PM | None Nov. 21, 2006 3:15 PM |
| X249-5T | SS | W 5.203 g loosely adhered coating | 1 × 20 × 34 mm | *Enterobacter Aerogenes* Nov. 20, 2006 2:19 PM | Swab collected after 3:00 (Hours:Mins) of BT on 11/20 5:19 PM | 78 F. (for first 16 h), 82 F. (16 h to 47 h) | None Nov. 21, 2006 8:20 AM & 1:30 PM | None Nov. 21, 2006 3:15 PM |
| X251-5T | SS | Fe No change in wt could be recorded because of the low sensitivity of the weigh scale | 1 × 23 × 34 mm | *Enterobacter Aerogenes* Nov. 20, 2006 2:20 PM | Swab collected after 3:00 (Hours:Mins) of BT on 11/20 5:20 PM | 78 F. (for first 16 h), 82 F. (16 h to 47 h) | None Nov. 21, 2006 8:20 AM & 1:30 PM | None Nov. 21, 2006 3:15 PM |
| X252-5T | SS | Ni + 0.001 g | 1 × 21 × 33 mm | *Enterobacter Aerogenes* Nov. 20, 2006 2:21 PM | Swab collected after 3:00 (Hours:Mins) of BT on 11/20 5:21 PM | 78 F. (for first 16 h), 82 F. (16 h to 47 h) | None Nov. 21, 2006 8:20 AM & 1:30 PM | None Nov. 21, 2006 3:15 PM |
| X253-5T | SS | Ti No change in wt could be recorded because of the low sensitivity of the weigh scale | 1 × 22 × 33 mm | *Enterobacter Aerogenes* Nov. 20, 2006 2:22 PM | Swab collected after 3:00 (Hours:Mins) of BT on 11/20 5:22 PM | 78 F. (for first 16 h), 82 F. (16 h to 47 h) | None Nov. 21, 2006 8:20 AM & 1:30 PM | None Nov. 21, 2006 3:15 PM |

TABLE 3A-continued

Microbial Test Results for Certain Coated and Uncoated Substrates

| Expt # | Substrate Material | Deposited Material | Sample size, mm | Bacterium treatment (BT), minutes | Swab collected | Temperature of Incubation, °F. | # of colonies at 15:00 & 20:00 hours of incubation. (MACRO Observation) | # of colonies at 22:00 hours of incubation. (MACRO Observation) |
|---|---|---|---|---|---|---|---|---|
| X254 | SS | None | 1 × 22 × 34 mm | *Enterobacter Aerogenes* Nov. 20, 2006 2:23 PM | Swab collected after 3:00 (Hours:mins) of BT on 11/20 5:23 PM | 78 F. (for first 16 h), 82 F. (16 h to 47 h) | None Nov. 21, 2006 8:20 AM & 1:30 PM | 2 Red dots of bacteria present Nov. 21, 2006 3:15 PM |

What is claimed:

1. A structure comprising: a substrate, and a porous coating applied to a surface of the substrate, wherein the coating comprises a plurality of partially sintered particles and wherein an average size of the particles is less than about 800 nm, wherein each of the particles at least partially adheres to at least one of the substrate or another one of the particles, wherein the particles that at least partially adhere to the substrate are fused to the substrate, wherein at least one portion of the substrate is covered by the coating, and wherein the coating exhibits antimicrobial properties resistant to chemical attack.

2. The structure of claim 1, wherein the coating is inorganic.

3. The structure of claim 1, wherein the structure is durable.

4. The structure of claim 1, wherein the coating comprises at least one of an oxide.

5. The structure of claim 1, wherein the coating comprises at least one of: a compound from the group of rare earth metal, $NiFe_yO_x$, $WO_x$, $FeMoS_x$, $FeC_x$, $Fe_zNO_x$, $SiO_x$, $MoSi_xAl_y$, and a further defect compound, where x, y, and z represent non-integer values.

6. The structure of claim 1, wherein the coating comprises at least one of: silicon carbide, siliconoxycarbide, silica, siliconoxynitrocarbide, ironsilicate, molybdenumcarbosilicide, and a further carbide.

7. The structure of claim 1, wherein the coating comprises at least one of: a phosphide, boride, silicide, aluminide, sulfide, nitride, oxide, and carbide.

8. The structure of claim 1, wherein at least one particle has a form of a nanotube.

9. The structure of claim 1, wherein at least one particle is metallic or semiconductive.

10. The structure of claim 1, wherein the coating comprises a first layer and a second layer, wherein the first layer has a first composition and the second layer has a second composition, and wherein the second composition is different from the first composition.

11. The structure of claim 1, wherein the coating has a thickness of less than about 2000 nm.

12. The structure of claim 1, wherein the coating has a thickness of less than about 800 nm.

13. The structure of claim 1, wherein the coating comprises a first layer and a second layer, wherein the first layer has a first average particle size and the second layer has a second average particle size, and wherein the second average particle size is different from the first average particle size.

14. The structure of claim 1, wherein the coating is to be formed by: producing an arc at a distal end of an electrode of an electrode arrangement which is configured to produce the arc without the distal end of the electrode being in proximity to an electrically grounded object, wherein the arc is configured to discharge particular particles from the electrode; and providing the substrate in a proximity to the arc, wherein the particular particles are provided on at least one of the substrate or other ones of the particular particles.

15. The structure of claim 14, wherein the particles comprise at least one of: silver, tungsten, iron, carbon, aluminum, copper, nickel, iron, SiC, $SiO_2$, an oxide of at least one of nickel, iron, tungsten, or chromium, Cu, Ag, Au, Pt, Pd, Ir, a rare earth metal, a semiconductor, B, Si, Ge, As, La, Sb, Te, Po, an iron oxide, a tungsten oxide, a chromium oxide, $V_2O_5$, $Fe_2O_3$, FeOx, $Fe_3O_4$, aluminum oxide, NiO, zinc oxide, tin oxide, hafnium carbide, tungsten carbide, $MnO_2$, $SiO_2$, $MoO_3$, $HfO_2$, $WO_3$, $TiB_2$, $CrO_3$, $Nb_2O_5$, $Al_2Zr$, $B_4C$, $SiO_x$, $ZrSiO_4$, $B_2O_3$, CdS, MnS, $MoS_2$, $NaN_3$, NaCN, $Si_2N_4$, PbO, $PbO_2$, $WO_2$, $BaO_2$, $SiO_x$, $NiFe_yO_x$, $MoS_x$, $Fe_2NO_x$, and a further defect compound, where x, y, and z represent non-integer values, or at least one of an oxide, a carbide, a nitride, an aluminide, a boride, a silicide, or a halide of at least one of Cu, Ag, Au, Fe, Si, Ti, Hf, Pt, Pd, or Ir.

16. The structure of claim 1 wherein each of the particles exhibits antimicrobial properties.

17. The structure of claim 1 wherein the coating has a high specific surface area.

* * * * *